United States Patent [19]

Stindl

[11] Patent Number: 5,017,605

[45] Date of Patent: May 21, 1991

[54] COSMETIC CREAM PREPARATION CONTAINING WATER/OIL AND OIL/WATER EMULSIONS

[75] Inventor: Wolfgang Stindl, Eisenstadt, Austria

[73] Assignee: Schering Wien Ges. m.b.H., Vienna, Austria

[21] Appl. No.: 388,752

[22] Filed: Aug. 3, 1989

Related U.S. Application Data

[63] Continuation of Ser. No. 74,173, Jul. 16, 1987, abandoned, which is a continuation of Ser. No. 815,498, Jan. 2, 1986, abandoned, which is a continuation of Ser. No. 614,926, May 29, 1984, abandoned, which is a continuation of Ser. No. 376,444, May 10, 1982, abandoned.

[30] Foreign Application Priority Data

May 8, 1981 [AT] Austria ................... 2071/81

[51] Int. Cl.$^5$ ............................. A61K 31/215
[52] U.S. Cl. ..................... 514/529; 514/506; 514/772; 514/938; 514/939; 514/943
[58] Field of Search .............. 514/772, 836, 938, 939, 514/943, 506, 529

[56] References Cited

U.S. PATENT DOCUMENTS 4,284,630  8/1981  Yu et al. .
4,348,415  9/1982  Tsutsumi et al. .

OTHER PUBLICATIONS

Matsumoto et al.—Chem. Abst., vol. 85, (1976), p. 182,720v.
Taguchi et al.—Chem. Abst., vol. 93 (1980), p. 101346t.
Kosmetika Aerosole Riechstoffe, 57 Jahrgang, Ausberg, Jun. 28, 1984, nr. 10–2. Juniheft CA 94:1453895.
Double Emulsions, Mixed Emulsions and Pseudoemulsions Die Emulsionen in Der Hauttherapie, S. Hitzel Verlag, Stuttgart, p. 23, 1951 (F. Schmidt-La Baume).
Brunnegger et al., Sci. Pharm. 53, 1985, pp. 223–236.
Test Report I, Test to rework AT-2071/81.
Viviane Brochure, translation of pp. 3 and 6–13.

*Primary Examiner*—Sam Rosen
*Attorney, Agent, or Firm*—Millen, White & Zelano

[57] ABSTRACT

A cosmetic preparation consists essentially of a mixture of a stable oil/water emulsion of cosmetically acceptable ingredients and a stable water/oil emulsion of cosmetically acceptable ingredients. The new preparation is prepared by mixing the two original emulsions such that a superfinely dispersed product is obtained. The particle size of the inner phases of the emulsions is 2–50 μm. The preparation provides needed ingredients such as fats or moisture to skin of varying types. An example of the cosmetic preparation is a cream containing jojoba oil.

13 Claims, No Drawings

COSMETIC CREAM PREPARATION CONTAINING WATER/OIL AND OIL/WATER EMULSIONS

This application is a continuation of Ser. No. 07/074,173, filed July 16, 1987, which is a continuation of Ser. No. 06/815,498, filed Jan. 2, 1986, which is a continuation of Ser. No. 06/614,926, filed May 29, 1984, which is a continuation of Ser. No. 06/376,444, filed May 10, 1982, all now abandoned.

BACKGROUND OF THE INVENTION

The present invention relates to a cosmetic preparation in the form of a salve, paste, cream or the like, which contains hydrophilic and/or lipophilic substances, a lipid phase, an aqueous phase, emulsifiers, preservatives and fragrances.

Numerous cosmetic creams, salves or the like of this kind are known. Particularly, these include the so-called nourishing and moisturizing creams, which are based on either an oil/water emulsion or a water/oil emulsion. The problem with such creams, however, is that the various different areas of the skin or different skin types which have different fat or moisture requirements, cannot have their specialized needs met with the application of creams of this type. Measured by their fat and/or moisture requirements, individual areas of the skin generally receive either too much or too little of one or more of the lipid phase, nutritional substances or moisture and the like when such a cream is applied. Furthermore, the application of various creams one after another, based first on the one and then on the other emulsion type, does not solve this problem.

SUMMARY OF THE INVENTION

Accordingly, it is an object of this invention to provide cosmetic salves, creams or the like, with which different areas of the skin can simultaneously be supplied with fat, nutritional substances and/or moisture in accordance with their specific needs.

Upon further study of the specification and appended claims, further objects and advantages of this invention will become apparent to those skilled in the art.

These objects have been attained, in one aspect, by providing a cosmetic preparation in the form of a salve, cream or the like, comprising hydrophilic and/or lipophilic substances, wherein the lipid phase and the aqueous phase are in the form of a superfinely dispersed mixture of an oil/water emulsion containing an oil/water emulsifier and preservatives and a water/oil emulsion containing a water/oil emulsifier.

In another aspect of this invention, these objects have been attained by providing a method for producing a cosmetic preparation in the form of a salve, paste, cream or the like, comprising producing an oil/water emulsion from the lipid phase, aqueous phase, oil/water emulsifier and preservatives, producing a water/oil emulsion from the lipid phase, aqueous phase and water/oil emulsifier, intimately stirring the two emulsions, with the addition of hydrophilic and/or lipophilic substances, in a vacuum at a temperature of 20° to 40° C., and then mixing the resultant finely dispersed mixture with fragrances.

DETAILED DISCUSSION

Using the cream containing the superfinely dispersed mixture of the two types of emulsions, there is produced on the skin an oil/water or water/oil hydrolipid film which is appropriate for that location of skin depending on its moisture content or skin type.

In accordance with this invention, "superfine" refers to a particle size of the emulsion mixture of from 2 to 50 $\mu$m.

Although in terms of the varying needs of the skin, it might appear to be obvious simply to mix the two types of emulsions in order to produce a cream which will satisfy such needs, in fact, this is not the case at least since, heretofore, no process was available for achieving such a combination. This is because the two emulsion types could heretofore not be kept in a stable form in the presence of each other; quite the contrary, depending on the components used, invariably, soon after preparation, at the latest, a conversion of one emulsion type into the other occurred. Thus, in the final analysis only one emulsion type actually remained in the cream thus produced.

Surprisingly, in accordance with this invention, if the two emulsion types are combined at a temperature of 20° to 40° C., preferably at about 30° C., in a vacuum, in a particularly gentle yet still very intensive manner in the container of a conventional stirring apparatus, such that a very fine dispersion of the two emulsions is finally attained, e.g., one whose particle size is 2 to 50 $\mu$m preferably 5 to 15 $\mu$m, then the two types of emulsions are maintained in the resultant cream. That is, they exist in one another's presence; yet are essentially unchanged in nature. This emulsion system remains stable even after substantial dilution, for instance with 50–250 wt. % of a liquid phase.

Without intending to limit this invention in any way, it is presumed that both the particle size and the cooperation of the emulsifiers are of significance for the stability of the emulsion system of this invention. It is essential that in producing the cosmetic preparation according to the invention, the emulsions are dispersed and not homogenized.

The two emulsions are united in a vacuum of, e.g., 0.5 to 100 torr, preferably 0.5 torr to 50 torr, the precise value not being critical. The appropriate stirring conditions such as stirring speed time, charge size etc., which can be used to achieve the necessary superfine intimate mixture, as is well known to one skilled in the art, are dependent on which of the available conventional stirring apparatus is used and can readily be ascertained in a manner known per se using routine preliminary experiments where necessary. Suitable stirrers are well known and discussed, e.g. in the references cited below. All stirrers suitable for the preparation of salves, creams or the like may be used for the inventive preparation.

The oil/water emulsions per se and the water/oil emulsions per se are fully conventional and can be produced in fully conventional manner, using conventional emulsifiers (See, e.g., Kirk Othmer, *Encyclopedia of Chemical Technology*, 3rd edition, 1979, John Wiley and Sons, New York etc., Vol. 8, pp. 900–930; and Dr. Otto-Albrecht Neumüuller, Rümpps Chemie Lexikon [Römpp's Chemistry Lexicon], 7th edition, 1973, Franck'sche Verlagshandlung, Stuttgart, pp. 1009–1013 whose disclosures are incorporated by reference herein). The waxes, emulsifiers and other ingredients employable in these emulsions and the relative amounts employed, are the same as those conventionally used for emulsified skin-care preparations (See, e.g., Dr. Otto-Albrecht Neumüller, *Rompps Chemie Lexikon*, 7th edition, 1972, Franck'sche Verlagshandlung, Stuttgart, pp.

1427 and 1427 which disclosure is incorporated by reference herein).

Suitable oil/water emulsions useful in the cosmetic preparation according to the invention can comprise hydrophilic and/or lipophilic substances, a lipid phase, an oil/water emulsifier, an aqueous phase and preservatives.

Suitable hydrophilic and/or lipophilic substances include moisture-retaining factors (hydrocomplexes), such as glycerine, polyethleneglycols or amino acids (preferably polyethyleneglycols or amino acid mixtures), Puroba oil (i.e., jojoba oil), vitamins (preferably vitamins A and E), vital complexes (for instance, placental extracts), enzymes, herbal extracts (for instance, hamamelis extract or camomile extract) or proteins (such as collagen, for example). Substances suitable as the oily or lipid phase in the oil/water emulsions include hydrocarbons such as Vaseline, paraffins or stearin, or waxes, such as beeswax. Examples of suitable oil/water emulsifiers include stearyl alcohol, polyoxyethylene stearates (such as MYRJ ®), complex emulsifiers (such as Amphoterin ®) and sorbitan fatty acid esters (for example, Span ®) or carboxyvinyl polymerizates (such as Carbopol ®). The aqueous phase can additionally contain buffer substances, such as the disodium salt of the ethylenediamine-N,N,N',N'-tetraacetic acid, and preservatives such as chloroquinaldol, Parabene or benzalkonium chloride.

In the oil/water emulsions, the proportion of the inner emulsion phase is preferably from 30 to 49% by weight; the particle size of the inner phase is preferably 1 $\mu$m to 100 $\mu$m. In the course of the further dispersion of the two phases, in accordance with this invention, these inner phase particles are once again comminuted and in the final product are of a size below 50 $\mu$m, as mentioned.

The water/oil emulsions usable in the cosmetic preparations according to this invention can comprise hydrophilic and/or lipophilic substances, such as those discussed in connection with the oil/water emulsions, a lipid phase, a water/oil emulsifier and an aqueous phase. Examples of substances suitable as the oily or lipid phase of the water/oil emulsion include hydrocarbons, such as paraffins and Vaseline, and synthetic, vegetable and animal oils or waxes (for instance, olive oil, peanut oil, fine bone oil, almond oil, lanolin, beeswax or sunflower oil). Purified demineralized water can be used as the aqueous phase of either type of emulsion. Substances which can be used as the water/oil emulsifier include wool fat (i.e., lanolin), fatty alcohols such as cetyl alcohol, myristyl alcohol, stearyl alcohol or ceryl alcohol, fatty acid esters, such as beeswax (cera alba) or waxy alcohol esters or mixed esters (for instance, Dehymuls ®).

In the water/oil emulsions, the, proportion of the inner emulsion phase is preferably 30 to 49% by weight. The particle size of the inner phase is also preferably 1 $\mu$m to 100 $\mu$m. In the course of the further dispersion of the two phases, in accordance with this invention, these inner phase particles are once again comminuted and in the final product are below 50 $\mu$m as mentioned.

The proportions of the oil/water emulsion and the water/oil emulsion in the mixture of this invention are 20 to 80% by weight and 80 to 20% by weight, respectfully, preferably 35 to 65% by weight and 65 to 35% by weight. The hydrophilic/lipophilic substances can be incorporated separately into each or one of the water-/oil and oil/water emulsions. Equivalently, the oil/water and water/oil emulsions can be produced without the hydrophilic/lipophilic substances or with only a portion of the finally desired amounts of such substances, and then, the desired full or remainder amount cf such substances can be incorporated into the final product of this invention as an additional component included in the charge of oil/water and water/oil emulsions which is superfinely mixed in accordance with this invention. The amounts of such hydrophilic/lipophilic substances will correspond to the conventional amounts contained in the oil/water and water/oil emulsions per se as discussed above.

The finely dispersed system which is subsequently produced by this invention can thus be conventionally mixed with the usual amounts of customary fragrances such as those of the Crematest ® series. Of course, the conventional blending method used must be compatible with the foregoing details of this invention, e.g., must not deleteriously affect particle sizes or stability.

The cosmetic preparations of this invention can be used for the same purposes and in analogous fashion to the use of the many conventional cosmetic preparations, including nourishing and moisturizing creams such as Nivea$^{(R)}$.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

The cosmetic preparation in the form of a nourishing cream of this invention may by way of example have the following composition:

|  |  | Tolerances |
|---|---|---|
| Puroba oil | 5% | 5-10% |
| cera alba (beeswax) | 1% | 1-5% |
| Dehymuls ® | 1% | 1-3% |
| stearyl alcohol | 4% | 4-8% |
| hydrocarbons | 30% | 30-50% |
| Carbopol ® | 1% |  |
| MYRJ ® | 3% | 2-5% |
| disodium edetate | 1% |  |
| chloroquinaldol | 1% |  |
| purified demineralized water | 52% | 30-55% |
| perfume oil | 1% |  |

The percentages given are by weight.
The following exemplary embodiments further show the method of this invention:

EXAMPLE 2

Production of an oil/water emulsion 10.00 g of disodium edetate and 10.00 g of chloroquinaldol are dissolved in 300.00 g of purified, demineralized water and mixed with 10.00 g of Carbopol ®.

This mixture is added, being stirred forcefully, to a melted mass of 80.00 g of Vaseline (DAB ®8), 40.00 g of stearyl alcohol, 30.00 g of MYRJ ® and 50.00 g of Puroba oil. The mixture is stirred until such time as an emulsion having a particle size from 20 to 70 μm has resulted.

DAB 8 is the abbreviation for the Deutsche Arzneibuch [German Pharmaceutical Manual], 8th edition, 1978.

EXAMPLE 3

Production of a water/oil emulsion 228.00 g of purified, demineralized water is added, being stirred forcefully, to a melted mass of 220.00 g of Vaseline (DAB 8), 10.00 g of Dehymuls ® and 10.00 g of cera alba. The mixture is stirred until such time as an emulsion having a particle size from 20 to 70 μm has resulted.

EXAMPLE 4

Production of a cream

The water/oil emulsion is added, being stirred forcefully, to the oil/water emulsion under a vacuum of 10 torr. The mixture is stirred until such time as a dispersion having a particle size from 10 to 50 μm has resulted; the vacuum is eliminated, and 2.00 g of a fragrance of the Crematest ® series is added while stirring.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cosmetic preparation having a cream-like consistency consisting essentially of a stable emulsion system containing a stable oil/water emulsion of cosmetically acceptable ingredients and a stable water/oil emulsion of cosmetically acceptable ingredients,
   wherein the identities of both said oil/water emulsion and said water/oil emulsion are maintained in said emulsion system, and
   wherein said cosmetic preparation contains jojoba oil.

2. A cosmetic preparation of claim 1, wherein the oil/water emulsion and water/oil emulsion are superfinely dispersed in said emulsion system.

3. A cosmetic preparation of claim 2, wherein the particle size of the inner phase of each emulsion is 2 to 50 μm.

4. A cosmetic preparation of claim 3, wherein the amounts of oil/water and water/oil emulsions are 20–80 wt %, and 80–20 wt %, respectively.

5. A cosmetic preparation of claim 3, wherein the oil/water emulsion comprises a lipid phase, an aqueous phase, and an oil/water emulsifier, all ingredients being cosmetically acceptable.

6. A cosmetic preparation of claim 5, wherein the oil/water emulsion further comprises a preservative and a hydrophilic/lipophilic substance, both being cosmetically acceptable.

7. A cosmetic preparation of claim 3, 5 or 6, wherein the water/oil emulsion comprises a lipid phase, an aqueous phase and a water/oil emulsifier, all ingredients being cosmetically acceptable.

8. A cosmetic preparation of claim 7, wherein the water/oil emulsion further comprises a hydrophilic/lipophilic substance which is cosmetically acceptable.

9. A cosmetic preparation of claim 3, wherein the proportion of the inner phase of each emulsion is 30–40% by weight of each of the oil/water emulsion and the water/oil emulsion.

10. A cosmetic preparation of claim 3, further comprising a cosmetically acceptable amount of a cosmetically acceptable fragrance.

11. A cosmetic preparation of claim 3, which is a salve, paste or cream.

12. A method of nourishing or moisturizing skin comprising applying thereto an effective amount of a cosmetic preparation of claim 1, whereby an oil/water or water/oil hydrolipid film is formed on a particular location of the skin in correspondence with its fat and moisture content.

13. A cosmetic preparation according to claim 1, wherein said preparation contains 5–10 wt. % jojoba oil.

* * * * *